US011944400B2

(12) United States Patent
Danieli et al.

(10) Patent No.: US 11,944,400 B2
(45) Date of Patent: Apr. 2, 2024

(54) ROBOTIC SYSTEM FOR ANGIOPLASTY AND ENDOLUMINAR SURGERY

(71) Applicants: CALABRIAN HIGH TECH S.R.L., Rende (IT); Guido Danieli, Rende (IT); Ciro Indolfi, Catanzaro (IT); Salvatore De Rosa, Calvizzano (IT)

(72) Inventors: Guido Danieli, Rende (IT); Ciro Indolfi, Catanzaro (IT); Salvatore De Rosa, Calvizzano (IT); Domenico Battaglia, Catanzaro (IT); Giovanni De Gaetano, Cosenza (IT); Gionata Fragomeni, Castrolibero (IT); Pasquale Francesco Greco, Carolei (IT); Gabriele Larocca, Polistena (IT); Michele Perrelli, Polistena (IT)

(*) Notice: Subject to any disclaimer, the term of this patent is extended or adjusted under 35 U.S.C. 154(b) by 1021 days.

(21) Appl. No.: 16/756,965

(22) PCT Filed: Oct. 26, 2018

(86) PCT No.: PCT/IT2018/050209
§ 371 (c)(1),
(2) Date: Apr. 17, 2020

(87) PCT Pub. No.: WO2019/082224
PCT Pub. Date: May 2, 2019

(65) Prior Publication Data
US 2021/0196412 A1   Jul. 1, 2021

(30) Foreign Application Priority Data

Oct. 26, 2017 (IT) .................. 102017000114767
Jan. 2, 2018 (IT) .................. 102017000151259
Oct. 11, 2018 (IT) .................. 102018000009380

(51) Int. Cl.
*A61B 34/37* (2016.01)
*A61M 5/00* (2006.01)
(Continued)

(52) U.S. Cl.
CPC ............. *A61B 34/37* (2016.02); *A61M 5/007* (2013.01); *A61M 25/0113* (2013.01);
(Continued)

(58) Field of Classification Search
None
See application file for complete search history.

(56) References Cited

U.S. PATENT DOCUMENTS 6,096,004 A    8/2000 Meglan et al.
9,731,096 B2 * 8/2017 Bian .............. A61M 25/09041
(Continued)

FOREIGN PATENT DOCUMENTS

WO    2011109283 A1   9/2011
WO    2012044334 A2   4/2012
(Continued)

OTHER PUBLICATIONS

International Search Report and Written Opinion for PCT/IT2018/050209 dated Dec. 2, 2019.
(Continued)

*Primary Examiner* — Manuel A Mendez
(74) *Attorney, Agent, or Firm* — Thomas | Horstemeyer, LLP (57) ABSTRACT

Robotic Angioplasty and Endoluminar Surgery System to separate patient and operator by remotely moving guides and catheters during operations, composed of three or more elements, of which at least one disposable (nose), available in different versions, like for independent advancements and retractions of a balloon catheter (or stent) and relative guide and to their common axial rotation, or for moving a guide
(Continued)

with a moving core or a catheter. The nose should be inserted into a non-sterile Slave placed near the patient, covered with sterile drapes, and with a combination of toothed wheels it translates all into three rotations controlled by three independent motors, possibly measuring the torque applied by the motors. By replacing the three angular gauges to the motors, a Master is obtained, controlled by a doctor by moving non-sterile tubes.

7 Claims, 7 Drawing Sheets

(51) Int. Cl.
| | |
|---|---|
| *A61M 25/01* | (2006.01) |
| *A61M 25/09* | (2006.01) |
| *A61M 25/10* | (2013.01) |
| *A61B 17/00* | (2006.01) |
| *A61B 34/00* | (2016.01) |
| *A61B 34/30* | (2016.01) |

(52) U.S. Cl.
CPC .......... *A61M 25/09* (2013.01); *A61M 25/104* (2013.01); *A61B 2017/0023* (2013.01); *A61B 2034/301* (2016.02); *A61B 2034/742* (2016.02)

(56) References Cited

U.S. PATENT DOCUMENTS

| | | | |
|---|---|---|---|
| 10,493,239 B2 * | 12/2019 | Hart | ........................ A61B 34/30 |
| 2014/0276392 A1 | 9/2014 | Wong et al. | |
| 2014/0296637 A1 | 10/2014 | Lee et al. | |
| 2020/0375682 A1 * | 12/2020 | Kincaid | ................. A61B 34/71 |

FOREIGN PATENT DOCUMENTS

| | | |
|---|---|---|
| WO | 2014053859 A2 | 4/2014 |
| WO | 2016097926 A1 | 12/2014 |

OTHER PUBLICATIONS

Search Report for Italian Patent Application No. 102017000114767 dated Aug. 28, 2018.

* cited by examiner

Figura 6

ROBOTIC SYSTEM FOR ANGIOPLASTY AND ENDOLUMINAR SURGERY

CROSS-REFERENCE TO RELATED APPLICATIONS

This application is a § 371 national phase application of PCT/IT2018/050209 filed Oct. 26, 2018 entitled "ROBOTIC SYSTEM FOR ANGIOPLASTY AND ENDOLUMINAR SURGERY," which claims the benefit of and priority to Italian Patent Application No. 102017000114767 filed Oct. 26, 2017, Italian Patent Application No. 102017000151259 filed Jan. 2, 2018, and Italian Patent Application No. 102018000009380 filed Oct. 11, 2018, the contents of which being incorporated by reference in their entireties herein.

BACKGROUND

The fact that minimally invasive techniques are continuously gaining momentum in medicine is well known. Among these increasing success collect those dedicated to angiography and angioplasty especially in lieu of the traditional surgery, which can take up to extracorporeal circulation and which are less well tolerated by the patient.

However, even these minimally invasive procedures carry a significant risk linked to exposure to ionizing radiation (which can induce cancer) not so much for the patient, who is exposed once in a while and gains an advantage, but the doctor who operates on the patient's side, even wearing the specific protections anti-radiation, is forced to receive an important daily dose of rays having to conduct the procedure, to handle guides and catheters within the vascular system of the patient directly at the table where X rays are applied. For this reason the firm Corindus (EP1755727B1, U.S. Pat. Nos. 7,615,042, D671,640, among others) created a robot that enables to guide the catheters during coronary procedures allowing both the catheter progress and the rotation by moving mouse and joystick. However, the method of handling joystick requires additional specific training to a doctor who instead has been trained to perform tasks manually operating directly on guides and catheters, resulting in use of additional time and financial resources. Moreover the system needs a major disposable component containing also engines, and is not flexible.

BRIEF SUMMARY OF THE INVENTION

A robotic system for angioplasty and endoluminar surgery is described including a console, comprising joysticks and buttons; an actuator to be placed near a patient comprising at least three motors, the actuator configured to control three degrees of actuation of the at least three motors; and a nose disposable element configured to contact with catheters and guide wires, thereby forcing their rotation, advancement, and retrieval within an artery or a vein of the patient; where the console may be driven by the joysticks and the buttons to move the catheters or the guide wires; where the actuator comprises at least three gears maintained coaxial by gears placed both externally and internally and separated by suitable bearings, of which a front one of the at least three gears holds the nose disposable element and a couple of bevel gears that are fixed to spur gears meshing with an internal toothing of a second one and a third one of the at least three gears, and mesh with bevel gears of the nose disposable element, so that turning the second one and the third one of the at least three gears will cause rotation of the bevel gears; where, while rotating at a same speed, the at least three gears will rotate the disposable nose element but not the bevel gears; and where the console is configured to compute and record amounts of the rotation, advancement, and retrieval.

A robotic system for angioplasty is described comprising the system described above, to which a plurality of syringe pumps are connected for distally controlling a contrast liquid injection.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views.

DETAILED DESCRIPTION

The initial idea of this system was instead to develop a new system whose basic mechanism should be able to function both as a measurement of penetration and rotation of the catheter, in the control section, master with an interface for the surgeon that reproduces a traditional operatory field, and, as an actuator of the same movements in the section of implementation, Slave, giving also the possibility of independent movement of guide and catheter, and introducing a small disposable component, while all the rest of the apparatus can also be used thousands of times. All this will be made possible thanks to the innovative working scheme described below.

In other words, the purpose of the present invention was to allow the separation of the doctor from the patient, with an innovative robot that uses the same basic mechanism to measure the movements of the doctor, and to actuate them, introducing guides and catheters into the vascular system of the patient. In this way the doctor can keep the patient under continuous radiographic control, without being affected by ionizing radiation, while operating in a way in he/she has been already trained. This is also foreseen in a Mitsubishi patent U.S. Pat. No. 6,096,004 to Corindus US.

However the reduced dimensions of the Slave and of the disposable component allowed the simultaneous use of more Slaves, for instance to guide the first catheter by coupling two slaves into a series, and also to allow control of two guide-catheter pairs by placing two in parallel and possibly one In series for the first catheter. But this possibility has induced us to develop a new Master Unit ad hoc.

Also note that different versions of disposables have been designed, to be described later on, together with the reasons that induced their development.

It should also be noted that thanks to the possibility of placing two Slaves in series, with the one next to the patient that controls the movement of the initial catheter, and the one behind which controls the movement of a guide with moving core, the system is practically able to reach any point in a patient's vascular system, which greatly amplifies its applicability well outside the angioplasty for which it was initially conceived. Finally, the system will also be able to allow doctors' training to traditional manual use, while allowing them to practice on previously recorded cases through an ambient in VR representing various scenarios and relative decision making options.

In practice, the system allows all the usual and unusual operations, being virtually configurable in the configuration preferred by the doctor for the particular case, all using small disposables not too expensive, of course one for Slave. Obviously all the advancements are independently controllable, and measured, so the system, for example, knows how much a catheter has penetrated, so it even knows, when retreating the catheter, how much it needs to call in order to be always controlled by the system. Among other things, it is possible to adjust the speeds of both feed and feedback, and it is possible to introduce contacts on the disposable element informing about the blocking or unlocking state of the transmission element (locked, guide the catheter, unlocked, leave it free), even if this can simply be detected by the operator simply observing the motion of the catheters inside the patient's body. It should also be noted that the separation operation between the guide and the catheter is in this case particularly simple. Of course remote controls both for the injection of contrast medium.

The basic idea was to measure rotations and advancement of the catheters made by the doctor and reproduce them on the patient, using two rotating systems virtually identical from a mechanical point of view, basically made by three hollow cylindrical gears, of which the first is used to measure the rotations imposed by the physician to the catheter, the second and the third to measure independently of the advancements of guide and catheter when this is needed.

Figure 1:
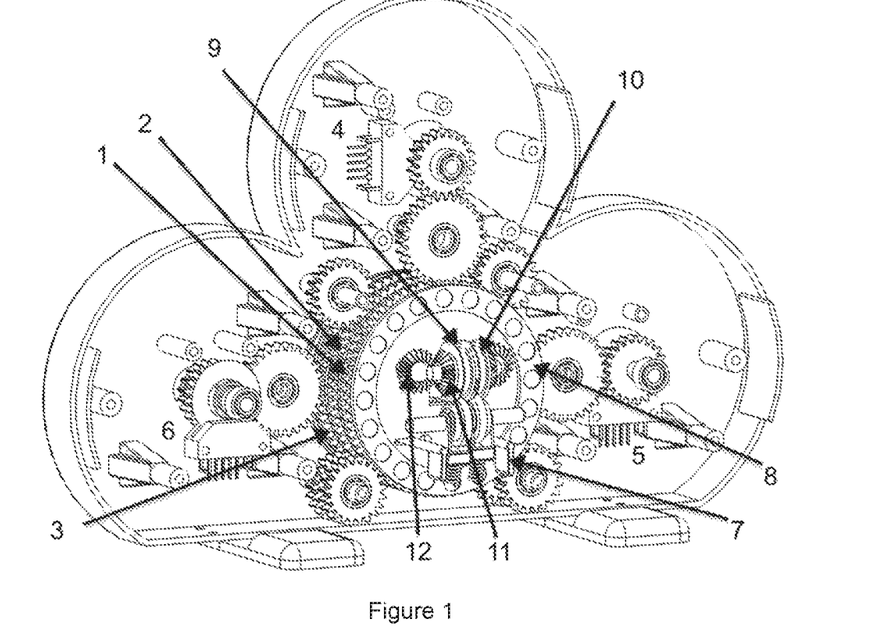
FIG. 1 shows a system that records or controls separately advances a guide catheter.

Referring to FIG. 1, which illustrates our basic system that records or controls separately advances of guide catheter, while rotations are common. We note that in the system there is a considerable number of gears of different sizes, while those at the center are three larger gears, of which the front one (1) records the rotations of the guide and catheter, while the subsequent ones (2) and (3) are dedicated to the separate recording of advances of guide and catheter. We should also note that there are three electronic components provided with pins (4) (5) and (6) that are connected, through an idle gear, to disks of lighter color that are no more than angular gauges. Also note that in front of the first gear is also positioned a first mechanism (7) which we will call the nose, containing four cylinders, two of which are integral with two other small bevel gears, and which is the only disposable element of the whole apparatus, in addition of course to guides, catheters, etc. The three measurement gears are kept in position by a system of gears consisting of three gears each, two small on one side, a larger one on the other side. These latter, idle, are dedicated, in the measuring robots next to the doctor, to transmit the motion to the system of measurement of the rotations of the hollow gears, while in the one next to the patient, to reproduce exactly the measured motion, while the two smaller are solely dedicated to keeping the two hollow gears coaxial. This system is then further kept in alignment is by a series of rings of balls, of which the first is shown by FIG. 1 (8), and by a system of toothed wheels inside the second and third wheel on which we shall return later.

Returning to the nose (7), of which several prototypes were developed, the standard model contains internally a system of friction wheels, of which the upper ones (9) and (10) are fixed and connected axially each to a bevel gear, of which is clearly visible only the (11), which mesh in turn with other two bevel gears of which only is visible as before (12), having an axis parallel to the system composed by the three main gears, but not coaxial to these. This gear (12), whose axis is integral with the front wheel, is then fixed to a second gear which will be shown later, which in turn meshes with an internal toothings integral with the second gear (2) placed behind the first one (1).

Figure 2:
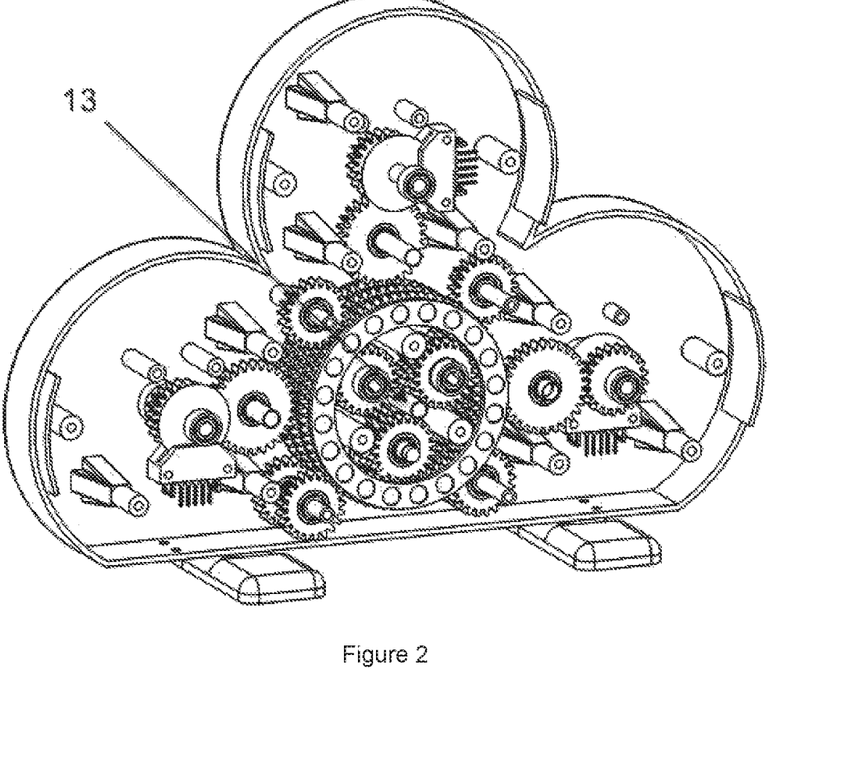
FIG. 2 shows the overall system of the gears and wheels seen from behind.

FIG. 2 then shows the overall system of the wheels seen from behind, eliminating the outer rear shell and putting in place the front one. Note how within the three main gears are present three other smaller gears, two of which are idle, while the third is fixed on the shaft which is connected to the bevel gear present on the opposite side. Note also that in the center there is a small diameter tube (4-6 mm) which is part of the nose (13), the only element disposable in the slave robot patient side, from which must pass and guide catheters, which must of course be kept insulated from all the mechanics, certainly not sterile.

Figure 3:
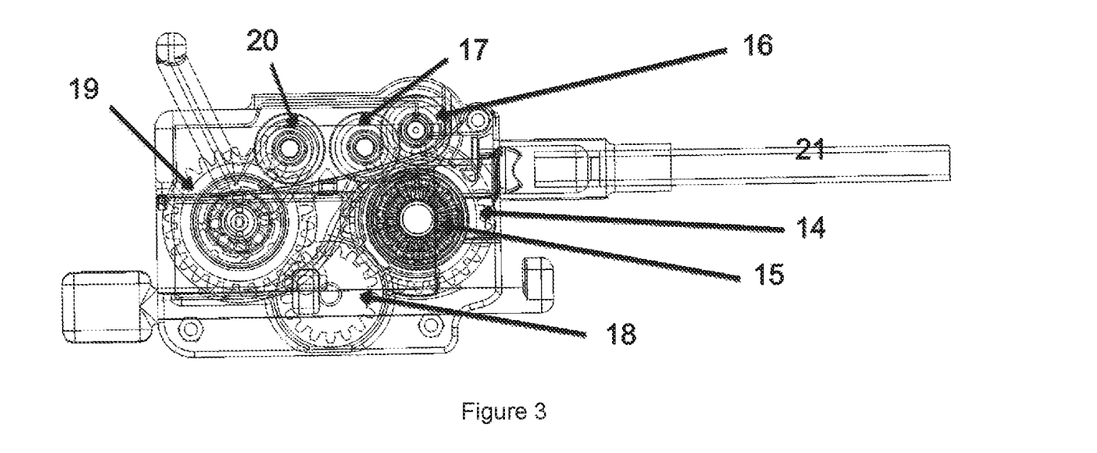
FIGS. 3-5 show a scheme of a nose dedicated to balloon catheters and related angioplasty guides of FIG. 1 in various views.
Figure 4:
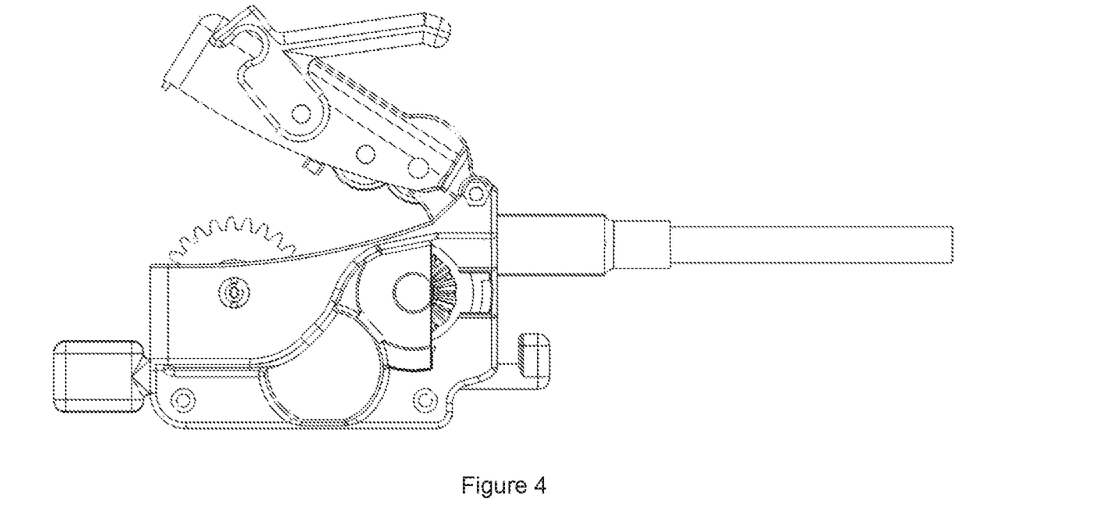
Figure 5:
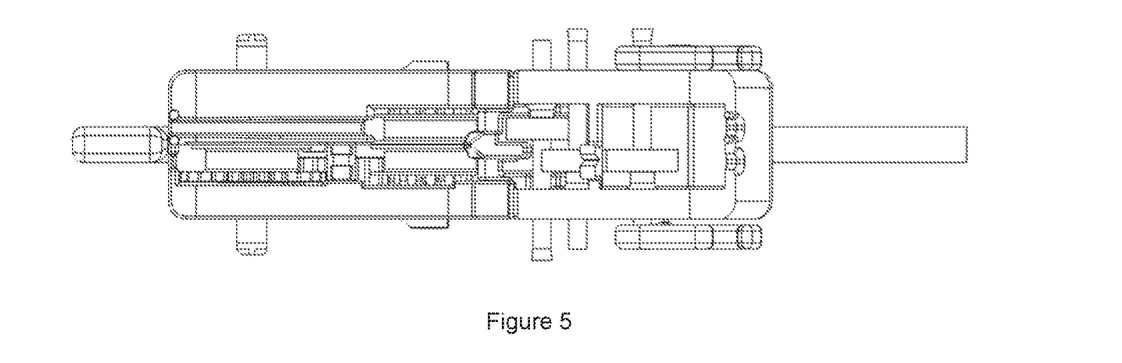

FIG. 3 shows a scheme of the nose dedicated to balloon catheters and related angioplasty guides (7) of FIG. 1 in lateral view, with transparent shell, closed, in motion transmission condition, and open for the displacement of the catheters, FIG. 4. Note how the lower wheels (to the right in this view, 14), integral with the conical wheels (15), each one are being compressed by an upper wheel, one of which (16) is located exactly on the vertical of the lower one, while the other (17) touches the lower wheel in a point moved to the right, being both loaded by the closure of the cover, locked by a hook. One of the two lower wheels, the one to transmit motion to the guide-wire, also presents toothing on the outside which engages with a second idle gear placed further down (18), which in turn meshes with an additional wheel toothed (19) fixed to a further friction wheel, in turn pressed by a further wheel (20) which touches the lower one at a point this time moved to the right. It should be noted that this apparent strangeness is due to the need to produce a curvature of the 0.014" guide to be able to transmit the twist to these guides which, due to the very small diameter, would not be transmitted unless this curvature was added. The lowered toothed wheels then serve to ensure that the feeds of the same guide are transmitted by all the wheels that lock it. The curvature was then calculated so as not to produce permanent deformations when driving. FIG. 5 shows the same open nose seen from above, in order to highlight how the catheter and the guide must be positioned on the nose, and how they can be easily moved from one side to the other. We must remember the procedure used to position the balloon catheters and the relative guides. Obviously it starts with an initial catheter and a guide, often introduced manually by highly experienced doctors. Naturally, these operations can also be carried out with two of our Slaves placed in series, obviously using a "nose" for each slave, in this case different from the one just described. Once the initial catheter is brought into place, the initial guide and its nose is extracted, and the nose for the balloon catheter and its guide are installed. At this point we introduce the 0.014" guide making it overcome the hemostatic valve, and, remotely (through the Master), the guide is brought into position. At this point the balloon catheter is introduced at the end of the guide and, as soon as the guide exits sideways from the catheter, it is blocked on a clamp placed at a suitable distance. Then the lid is opened and the catheter is flushed manually making it pass the hemostatic valve until the catheter and guide are separated again. At this point the catheter is placed on the left side of the nose and the guide on the right one, the nose cover is closed, and the movement control goes back to the Master.

Figure 6:
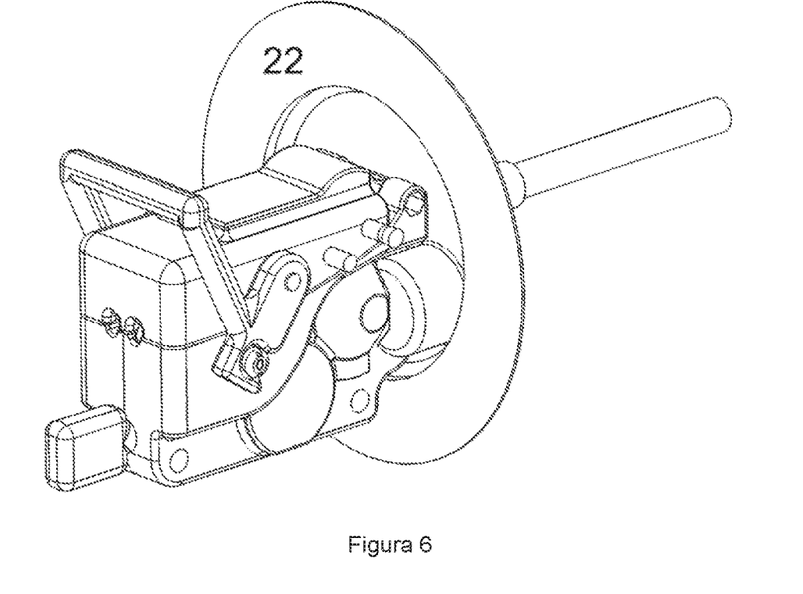
FIG. 6 shows a disk to be supplied with the nose, with the nose system mounted.

Note also that both the upper and lower wheels contain a micro ball bearing in order to reduce friction. In addition, the wheels are covered by O-rings to increase the friction between the wheels and the catheter. Finally, note from the back, the presence of a tube (21) that serves to isolate catheters and guides from internal mechanisms, ensuring sterility. Finally, still on the subject of sterility, a special disk has been designed that covers the entire central wheel so as to allow the whole apparatus to be covered with a sterile cloth, but allowing the rotation of the nose itself without allowing the whole cloth to be dragged. This disk (22), to be supplied with the nose, is shown in FIG. 6, with the nose system mounted.

Obviously for the first catheter, which has a much larger diameter, there will also be a simpler nose, in which the whole part dedicated to the 0.014" guide will not be present.

Moving instead to the description of how the nose is made for moving a guide with moving core, we begin to notice that if it is necessary to use a guide with moving core, it is also necessary to drive an initial catheter at the same time, and certainly not a balloon. Therefore in this case, as mentioned also in the introductory part, a first slave placed closest to the patient should be used, with which the progression, retraction and rotation of the initial catheter will be controlled, while with a second slave, the mobile core guide will be operated, which will be able to advance and rotate completely independently of the initial catheter, thus also varying the penetration of the core into the guide. Recalling that a Slave is able to simultaneously control three movements, rotation of the assembly and independent driving and catheter advances, we understand that it is possible to use rotation and advancement of the guide, but movement of the guide core with the third available movement. It is therefore only a matter of making a new nose that can do this, as described hereinafter. Naturally, it will also be necessary to give the master joystick the possibility of controlling a third movement. But this is easy, just use one that provides a third degree of freedom in addition to the usual backward, left-right.

Figure 7:
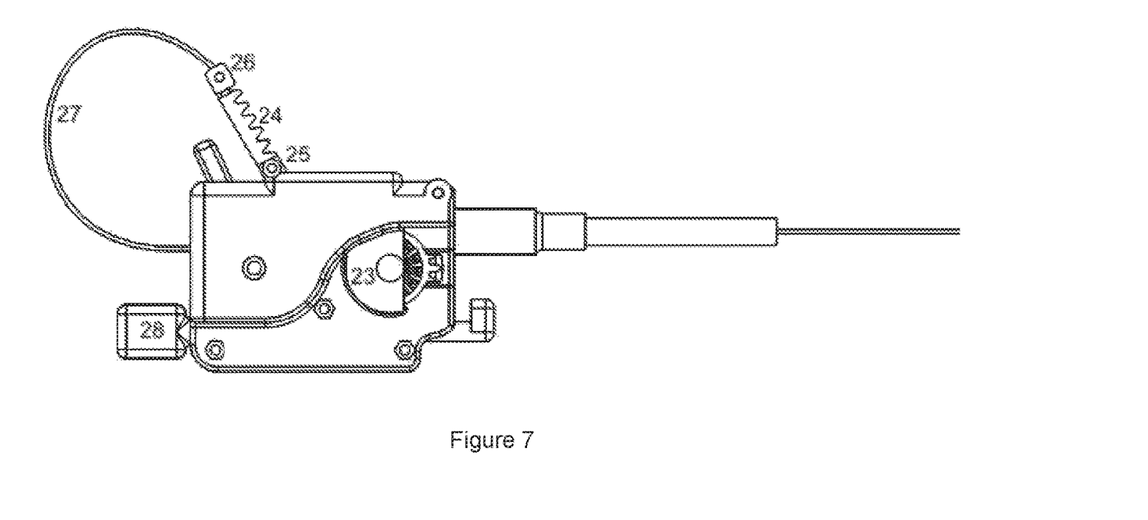
FIG. 7 shows a solution for a new nose in which a right side of the nose causes the guide to advance and retract.

FIG. 7 then shows the solution for the new nose in which, as usual, the right side of the nose causes the guide to advance and retract, on the left side the conical wheel that meshes with the corresponding wheel of the slave is connected not to a friction wheel, but to a small gear (23) which engages with a rack (24) which can slide in an oblique direction with respect to the axis of the nose. By connecting the extractable tail of the guide to the nose itself (25) and the rack guide body (26), naturally keeping the tail of the guide perfectly aligned with the direction of movement of the rack, we obtain control of the movement of the core with respect to the guide. Of course this will result in the generation of a curvature of over 180 degrees of the guide in its initial part (27), but if the guide is long enough this will not entail any problem. It should be noted, however, that this system, lockable to the Slave with a suitable key (28), thanks to the possibility of acting from afar on the guide's core, allows practically reaching almost any area of the body, obviously with extreme difficulty if you want to reach the brain given the presence of the cranial case, unless new visualization methods are discovered.

Figure 8:
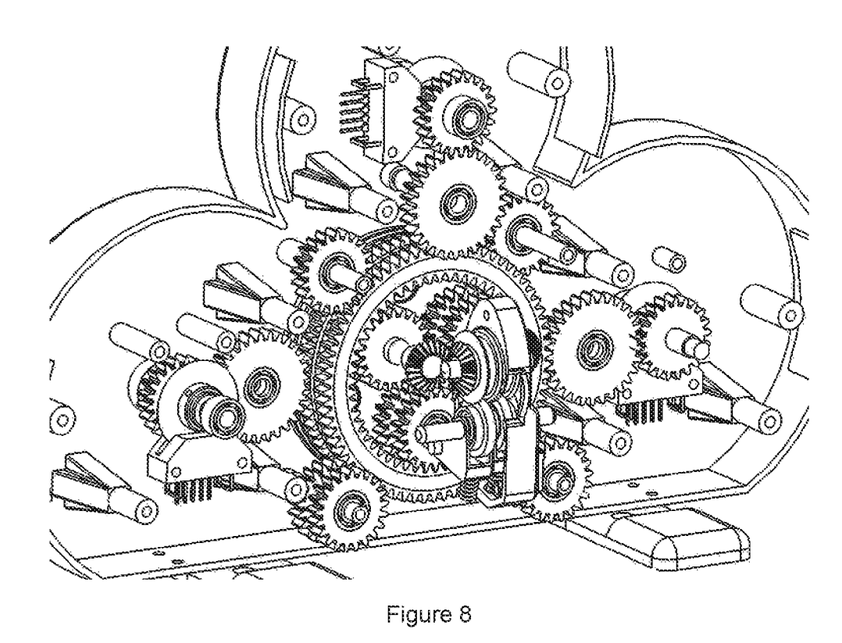
FIGS. 8 and 9 show a flow of actuation of the two rollers of the nose.
Figure 9:
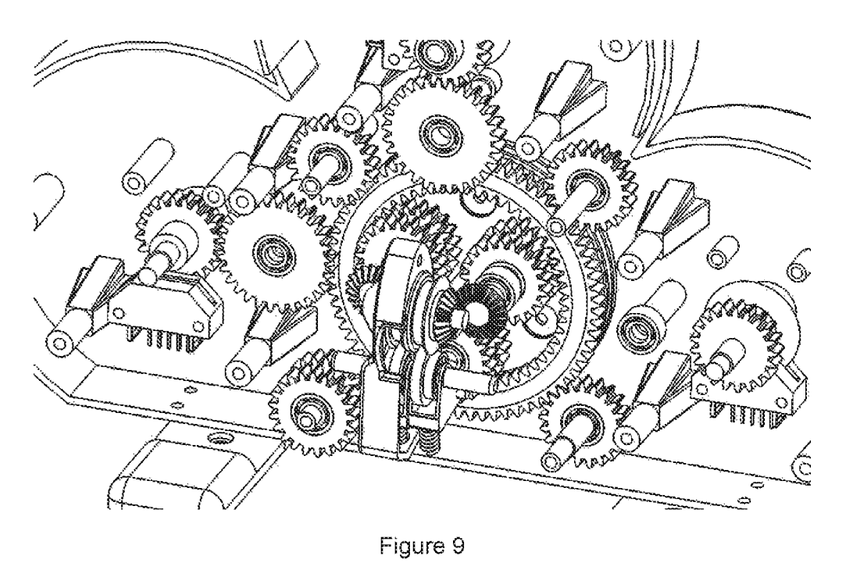

To better illustrate how the advancements are measured, the FIGS. 8 and 9 show the flow of actuation of the two rollers of the nose, in which are highlighted the organs handled by coloring in blue those linked to the roller to the left in front view, and green the ones connected to the roller to the right always in view fontal. In particular, note in FIG. 8, as the spur gear (29) which meshes with the one connected to the friction wheel to the left (30) is keyed on the same axis with a second cylindrical gear (31) which meshes with the internal toothings of the gear (22), which coincides with the gear (2) of FIG. 1. Turning to FIG. 9, a further bevel gear (33) meshes with the one connected to the right friction wheel (34), fixed on the same axis of a further gear (35) which meshes with the internal toothings of the gear (36), which coincides with the wheel (3) of FIG. 1.

Consequently, if you manage to get the right friction between the wheels and the catheter, simply record the rotations of the three wheels of the mechanism driven by the doctor, playing them on the one connected to the patient, a coronary angiography can be conducted at a distance. In fact turning on its axis the catheter, or more simply directly acting on the nose, turns the first gear (1) by dragging however also the two other coaxial gears (2) and (3) by means of the gear (29) for the (2) and (33) for (3). Conversely pushing the catheter or guide on the left side of the nose, you rotate the wheel (9) which, via the bevel gear (11) and (12) transmits the rotation to (29) which causes the rotation of (2). Similarly takes place for the advancement of the catheter or guide on the right side of the nose from the wheel (33) to (3). However, since the movements are combined, it is sufficient to record the rotations on the measuring robots to reproduce them on the slave to obtain the system operation. However, it is also possible to accelerate or decelerate the advancement movements recorded on the master, since it is sufficient to subtract the recorded motion from the main wheel to obtain the value of pure advancement, which can be multiplied or divided by the desired factor, adding the result to the rotation movement to obtain precisely the new value.

Figure 10:
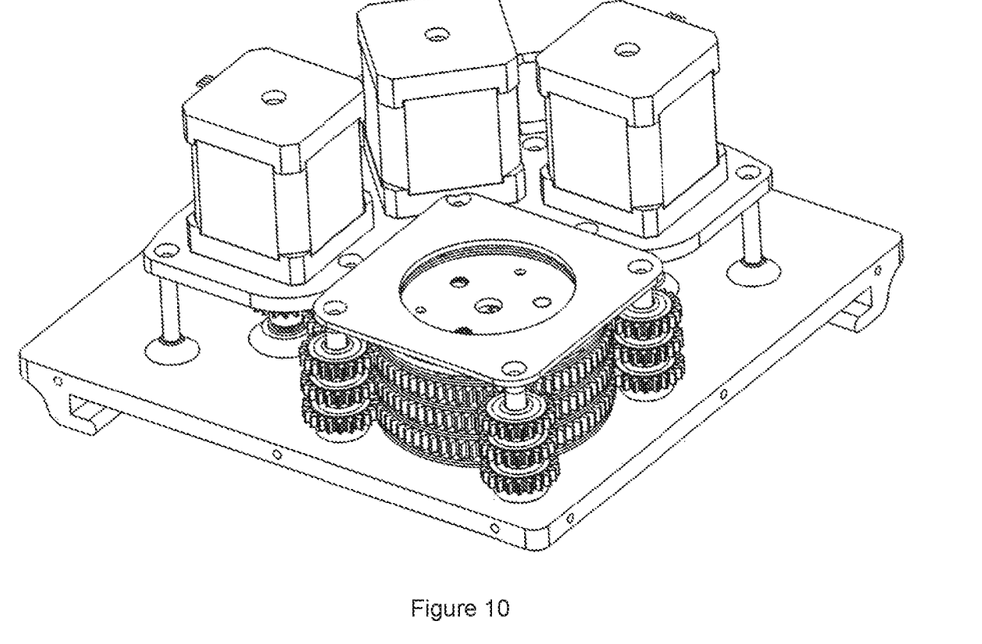
FIG. 10 shows the overall actuating (slave) system.

The subsequent FIG. 10 shows the overall actuating (slave) system, in which are added to the encoders the motors, in this case mounted parallel to the gearing system, exploiting their reduced length. Also note the asymmetric configuration with respect to the ones previously shown, used to minimize distance between the noses when is necessary to mount the slaves in parallel, as will be shown later on. It is also possible to mount the motors on a tilting system with torsional meter, to allow the recording of the advancement effort.

Resistance to advancement will be shown as a column of varying height on the screen, initially green, which becomes red if the effort exceeds certain levels, which will naturally be calibrated carefully.

Figure 11:
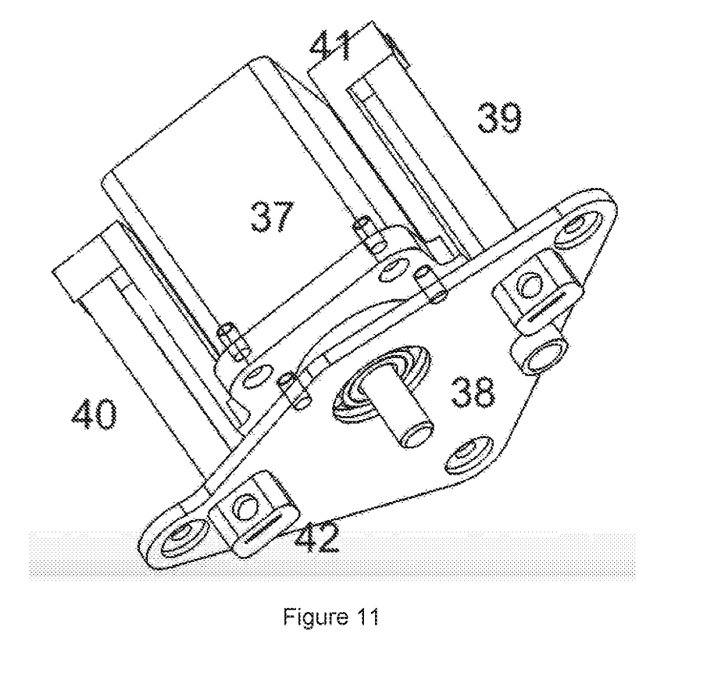
FIG. 11 shows detail of a measuring system of the delivered torque, when a motor is bearing-mounted coaxially to the shaft of motor and encoder.

FIG. 11 shows the detail of a possible measuring system of the delivered torque, when the motor (37) is bearing-mounted coaxially to the shaft of motor and encoder (38), while two side thin bars (39 and 40) connect the case motor (41) to the fixed frame (42), deforming in proportion to the transmitted torque, in order to record it by means of strain gauges.

As for the injection of contrast fluid, one may use a syringe pump with commercial remote control.

Figure 12:
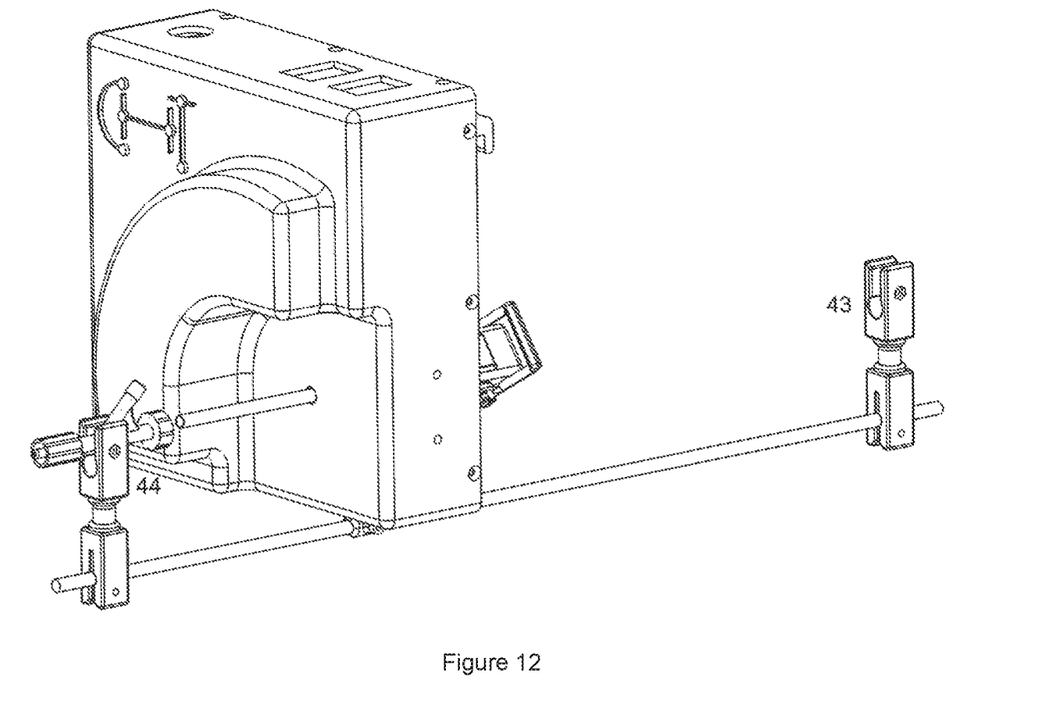
FIG. 12 shows the slave being attached to a small rod to hold away a clamp that grabs the guide-wire covered by two disposable sterile items.

It should also be noted that in order to allow the guide-wire to be blocked during the introduction of the balloon catheter, it is envisaged to attach to the slave a small rod to hold about 25 cm away a clamp (43), FIG. 12, which will grab the guide-wire covered by two disposable sterile items. On the opposite side of the slave is then provided with a second clamp (44) to grab the two-way blood flow locking tap and injection of the contrast fluid, which will be grabbed by wrapping the tap in the sterile cloth.

About the possibility of utilizing two slaves also to introduce the first catheter, in is enough to place the second slave in front of the first (45, closer to the patient). In this case the nose will be made for a single catheter of bigger diameter that the balloon ones. In the first slave (46, behind) the guide-wire must be positioned so that it can be moved within the first catheter, and also in this case the nose will be different, such the one shown in FIG. 7.

Figure 13:
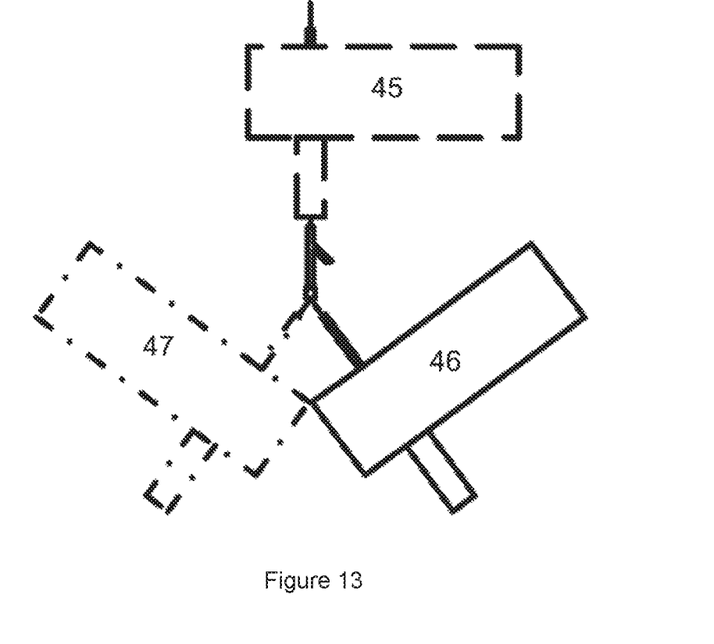
FIG. 13 shows multiple slaves placed in parallel due to their asymmetric configuration.

And yet, if you want to use two guides and two balloon catheters, the two slaves can be placed in parallel (thanks to their asymmetric configuration, FIG. 13), that shows from above the positioning scheme of the three slaves of which one can be mounted in front of the catheter to control the introductory catheter (dashed line, 45). Behind is placed (continuous line, 46) the slave that will be initially used for the initial guide, much bigger of the one used with the balloon catheter, where always with continuous line, is indicated also the hemostatic faucet with contrast liquid inlet. On the left (dashed and dotted line, 47)) may be placed the second slave for balloon catheters. Also note that the entire system is designed to be mounted both on the right and left side of the patient.

Figure 14:
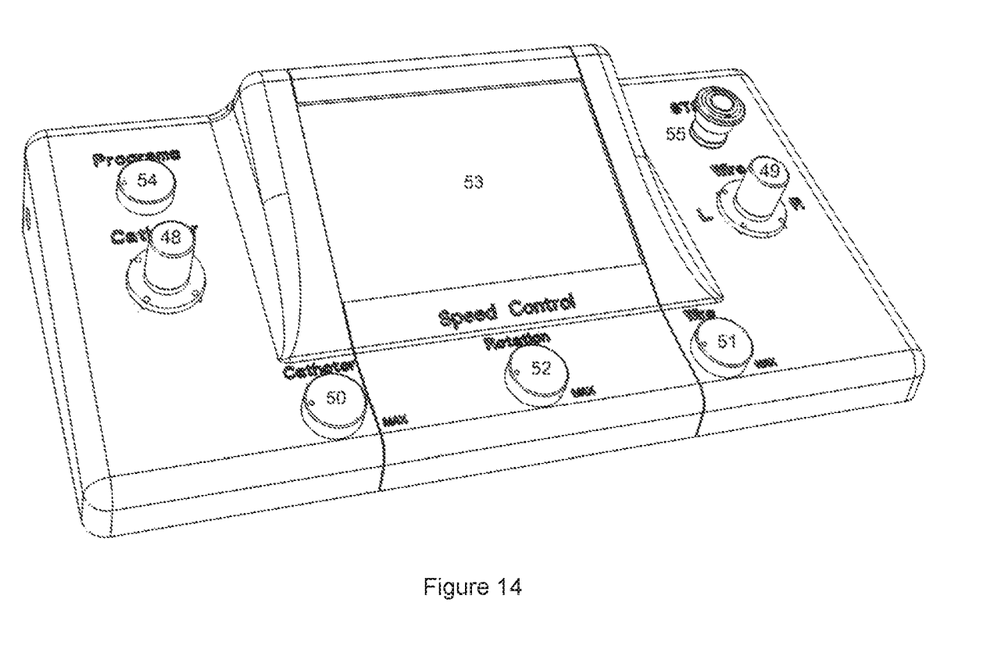
FIG. 14 shows an example of the system including two joysticks with a third rotating command.

Of course, you can use only one master to guide all the operations, adding to the master a selector to choose which slave must be activated from time to time. This however does not allow independent control of two slaves, as necessary when one wants to use the system also for the introduction of the initial catheter and relative guide-wire, whose rotations must be independent. This induced to study a joystick Master to replace the catheter Master that, even if not necessarily sterile, is in any event less flexible. The catheter Master will be available in any event for training for conventional operation, associating in to a VR representation of the operatory field. Obviously the same software will be available also in conjunction with the joystick Master. FIG. 14 shows the system designed. In particular the two joysticks (48) and (49) are both bilinear, with the addition of a third rotating command on top. Below each joystick rotating command (50) and (51) (could be substituted by sliders) allow regulating the advancement/retraction speed, while in between a third rotating command (52) allows regulating the speed of nose rotation. At the center, a display (53) presents the motion data that are also transmitted to a PC through a USB port, on the left side of it a selector (54) allows to chose the program, while on the right a red safety button (55) turns power off.

Passing to discuss the possible programs selectable with switch (54):

In option 1, the left joystick will command the rotations of the nose of the slave closer to the patient (dashed line in FIG. 13) when moved in the transverse direction, while it will control the advances of the only channel present on the nose dedicated to the initial catheter. At the same time, the right joystick will drive the feeds and rotations of the guide in the right channel of the nose of the slave on the right (continuous line) in the same way, while turning the top button on the right joystick will move the guide's core. And of course this will be clearly shown on the display of the Master.

In option 2, the left joystick will control the advancements of the catheter placed in the left channel of the nose present in the slave behind on the right (continuous line), while the right joystick will command the feeds of the guide and the guide and catheter rotations.

In option 3, the system will command the third slave (dashed dotted lines)) in the previous modes. Obviously then the final choice of channels to be used will be made in concert with the doctors.

Ultimately the system can be configured in practically many different versions, depending on the type and difficulty of the procedure to be performed.

Among the various options of this system, it will also be possible to add a second catheter Master to be used in parallel to the main one for the tutoring of young operators, who obviously have the possibility to take control in case of need, something that can also be done by a second console.

Another option, combining the use of a Master to a simulation in VR environment for the pre-clinical training of the operators, and, as a further option, the system could also be used for non-coronary procedures, with new noses and new programs.

Finally, the system, being usually connected to a personal computer (PC), may be used also as a kind of black box of the surgery, since it is able to register and store the entire procedure, eventually adding also the patient's pulsations, in order to provide complete documentation of what has been done, thus increasing the security of the procedure. This last solution is also useful for developing an advanced process risk management process. In summary, all procedural data may be re-evaluated in case of certain complications, thus helping the operator to recognize any complicating or facilitating factors, also allowing for specific restrictions on driving or catheter movements (e.g., avoiding the guide is inadvertently pushed forward too fast and/or too advanced with respect to the catheter).

The invention claimed is:

1. A robotic system for angioplasty and endoluminar surgery, comprising: a console, comprising joysticks and buttons;
   an actuator for placement near a patient comprising at least three motors, the actuator configured to control three degrees of actuation of the at least three motors; and
   a nose disposable element configured to come into contact with at least one of a catheter and a guide wire, thereby forcing rotation, advancement, and retrieval of the catheter or the guide wire within an artery or a vein of the patient;
   wherein the console may be driven by the joysticks and the buttons to move the catheter or the guide wire;
   wherein the actuator comprises at least three gears maintained coaxial by gears placed both externally and internally and separated by suitable bearings, of which a front one of the at least three gears holds the nose disposable element and a couple of bevel gears that are fixed to spur gears meshing with internal teeth of a second one and a third one of the at least three gears, and mesh with bevel gears of the nose disposable element such that turning the second one and the third one of the at least three gears will cause rotation of the bevel gears;
wherein, while rotating at a same speed, the at least three gears will rotate the nose disposable element but not the bevel gears; and
wherein the console is configured to compute and record amounts of the rotation, advancement, and retrieval.

2. The robotic system for angioplasty and endoluminar surgery according to claim 1, wherein:
the nose disposable element causes movement of a guide which forces the guide to form a double curvature delimited by an arc of a circle resulting compressed between four friction wheels, the four friction wheels comprising a first, second, third, and fourth friction wheel;
the first friction wheel is connected by a bevel gear to a slave mechanism, while the fourth friction wheel is connected through gears to the first friction wheel through an idler gear to preserve a direction of rotation so as to force transmission of torsion to the guide without causing permanent deformations; and
a part dedicated to movement of the catheter has a linear pattern, such that the catheter is compressed between two of the four friction wheels, one of which being the first friction wheel connected by the bevel gear to the slave mechanism while being controlled by a second motor, the second friction wheel being mounted on a vertical of the first friction wheel.

3. The robotic system for angioplasty and endoluminar surgery according to claim 2, wherein:
the nose disposable element comprises a movable core that presents, next to the bevel gear which connects the nose disposable element to the slave mechanism, a spur or a helical gear that engages with a rack, fixed to a small clamp that tightens the guide, while a fixed clamp tightens the head of the core such that acting on the bevel gear causes the movable core to be moved inside the guide to modify an initial curvature radius of the guide.

4. The robotic system for angioplasty and endoluminar surgery according to claim 1, wherein:
the joysticks are at least two bilinear joysticks, one of which being equipped with an input device to be controlled with one hand of an operator, the three motors of a slave, when needed, so as to handle an introduction of an initial catheter and its guide wire with or without movable core, in which case the slaves are put into series, or even use a second slave placed in parallel to allow the use side by side of two balloon catheters and their guiding wires, or even three slaves one of which in front for the introduction of the initial catheter, and two behind to guide the pair of balloon catheters, selecting from time to time through the central controller which catheter or guide wire to drive.

5. The robotic system for angioplasty and endoluminar surgery according to claim 1, wherein restrictions are imposed on movements of the catheter and the guide wire that prevent the guide being inadvertently pushed forward too quickly or too far.

6. A robotic system for angioplasty comprising the system of claim 1, to which a plurality of syringe pumps are connected for controlling distally a contrast liquid injection.

7. A method, comprising: providing a robotic system for angioplasty and endoluminar surgery, comprising: a console, comprising joysticks and buttons; an actuator for placement near a patient comprising at least three motors, the actuator configured to control three degrees of actuation of the at least three motors; and a nose disposable element configured to come into contact with at least one of a catheter and a guide wire, thereby forcing rotation, advancement, and retrieval of the catheter or the guide wire within an artery or a vein of the patient; wherein the console may be driven by the joysticks and the buttons to move the catheter or the guide wire; wherein the actuator comprises at least three gears maintained coaxial by gears placed both externally and internally and separated by suitable bearings, of which a front one of the at least three gears holds the nose disposable element and a couple of bevel gears that are fixed to spur gears meshing with internal teeth of a second one and a third one of the at least three gears, and mesh with bevel gears of the nose disposable element such that turning the second one and the third one of the at least three gears will cause rotation of the bevel gears; wherein, while rotating at a same speed, the at least three gears will rotate the nose disposable element but not the bevel gears; and wherein the console is configured to compute and record amounts of the rotation, advancement, and retrieval.

* * * * *